United States Patent
Kim et al.

(10) Patent No.: US 10,743,835 B2
(45) Date of Patent: Aug. 18, 2020

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Ji-han Kim, Hongcheon-gun (KR); Jae-keun Lee, Hongcheon-gun (KR); Gil-ju Jin, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 450 days.

(21) Appl. No.: 14/753,181

(22) Filed: Jun. 29, 2015

(65) Prior Publication Data

US 2016/0058410 A1 Mar. 3, 2016

Related U.S. Application Data

(60) Provisional application No. 62/044,374, filed on Sep. 1, 2014.

(30) Foreign Application Priority Data

Dec. 10, 2014 (KR) .................... 10-2014-0177827

(51) Int. Cl.
*A61B 8/06* (2006.01)
*A61B 8/08* (2006.01)
*A61B 8/00* (2006.01)

(52) U.S. Cl.
CPC ............... *A61B 8/06* (2013.01); *A61B 8/461* (2013.01); *A61B 8/467* (2013.01); *A61B 8/488* (2013.01); *A61B 8/5207* (2013.01); *A61B 8/5246* (2013.01)

(58) Field of Classification Search
None
See application file for complete search history.

(56) References Cited

U.S. PATENT DOCUMENTS 4,489,726 A * 12/1984 Epstein .............. A61B 5/02411
600/300
4,848,354 A * 7/1989 Angelsen ................. A61B 8/06
600/441

(Continued)

FOREIGN PATENT DOCUMENTS

| CN | 1549933 A | 11/2004 |
|---|---|---|
| CN | 1559346 A | 1/2005 |
| CN | 101210966 A | 7/2008 |
| CN | 101404941 A | 4/2009 |
| CN | 102078202 A | 6/2011 |
| CN | 102387747 A | 3/2012 |
| CN | 102525563 A | 7/2012 |

(Continued)

OTHER PUBLICATIONS

Communication dated Jan. 27, 2016 issued by European Patent Office in counterpart European Patent Application No. 15165928.1.

(Continued)

*Primary Examiner* — Joanne M Hoffman
(74) *Attorney, Agent, or Firm* — Sughrue Mion, PLLC

(57) ABSTRACT

Provided are an ultrasound diagnosis apparatus and method of operating the same. The ultrasound diagnosis apparatus includes: a data acquisition unit configured to acquire flow data in real-time from a region of interest (ROI) of an object; a parameter setting unit configured to analyze a change in blood flow based on the flow data acquired in real-time and set a parameter according to the analyzed change in blood flow; an image generator configured to generate a color flow image of the ROI by applying the set parameter to the flow data; and a display configured to display the color flow image.

11 Claims, 8 Drawing Sheets
(3 of 8 Drawing Sheet(s) Filed in Color)

(56) References Cited

U.S. PATENT DOCUMENTS

| | | | | |
|---|---|---|---|---|
| 5,078,146 A * | 1/1992 | Sato | G01S 15/8979 | 600/440 |
| 5,103,827 A * | 4/1992 | Smith | A61B 8/06 | 128/DIG. 13 |
| 5,105,817 A * | 4/1992 | Uchibori | G01S 15/8979 | 600/454 |
| 5,190,044 A * | 3/1993 | Kawasaki | G01S 15/582 | 600/441 |
| 5,322,066 A * | 6/1994 | Miyataka | G01N 29/0609 | 600/437 |
| 5,348,015 A * | 9/1994 | Moehring | A61B 8/06 | 600/453 |
| 5,394,874 A * | 3/1995 | Forestieri | G01S 15/58 | 600/441 |
| 5,471,990 A * | 12/1995 | Thirsk | G01S 7/52071 | 600/455 |
| 5,479,926 A * | 1/1996 | Ustuner | G01S 7/52026 | 348/224.1 |
| 5,513,640 A * | 5/1996 | Yamazaki | G01N 29/0609 | 600/451 |
| 5,524,629 A * | 6/1996 | Mahony | G01S 7/52071 | 600/454 |
| 5,606,972 A * | 3/1997 | Routh | G01S 15/8979 | 600/455 |
| 5,623,930 A * | 4/1997 | Wright | A61B 8/06 | 600/445 |
| 5,709,211 A * | 1/1998 | Machida | A61B 8/06 | 600/454 |
| 5,860,928 A * | 1/1999 | Wong | G01S 7/52071 | 600/453 |
| 5,921,931 A * | 7/1999 | O'Donnell | A61B 8/06 | 382/162 |
| 6,006,128 A * | 12/1999 | Izatt | A61B 5/0066 | 600/476 |
| 6,017,309 A * | 1/2000 | Washburn | G01S 7/52071 | 600/454 |
| 6,023,968 A * | 2/2000 | Spratt | G01F 1/663 | 73/204.14 |
| 6,030,344 A * | 2/2000 | Guracar | A61B 8/08 | 600/447 |
| 6,039,690 A * | 3/2000 | Holley | A61B 8/14 | 600/440 |
| 6,059,729 A * | 5/2000 | Stonger | G01S 7/52026 | 382/128 |
| 6,086,539 A * | 7/2000 | Guracar | A61B 8/08 | 600/443 |
| 6,120,451 A * | 9/2000 | Washburn | G01S 7/52034 | 600/454 |
| 6,162,176 A * | 12/2000 | Washburn | G01S 7/52026 | 600/454 |
| 6,500,125 B1 * | 12/2002 | Muzilla | G01S 7/52026 | 600/454 |
| 7,846,098 B2 | 12/2010 | Bakircioglu et al. | | |
| 8,425,422 B2 * | 4/2013 | Srinivasan | A61B 8/00 | 382/128 |
| 8,971,600 B2 | 3/2015 | Yoshikawa et al. | | |
| 9,125,578 B2 * | 9/2015 | Grunwald | A61B 5/04017 | |
| 9,319,633 B1 * | 4/2016 | Birkenes | G01S 15/04 | |
| 9,532,724 B2 * | 1/2017 | Grunwald | A61B 5/0006 | |
| 9,662,088 B2 * | 5/2017 | Pelissier | A61B 8/06 | |
| 2002/0091319 A1 * | 7/2002 | Moehring | A61B 8/06 | 600/454 |
| 2003/0032869 A1 * | 2/2003 | Muramatsu | A61B 5/022 | 600/300 |
| 2003/0045797 A1 | 3/2003 | Christopher et al. | | |
| 2003/0149358 A1 * | 8/2003 | Maskil | A61B 8/06 | 600/437 |
| 2004/0087856 A1 * | 5/2004 | Panda | G01S 7/52046 | 600/443 |
| 2004/0102706 A1 | 5/2004 | Christopher et al. | | |
| 2005/0131300 A1 * | 6/2005 | Bakircioglu | A61B 8/06 | 600/453 |
| 2005/0156593 A1 * | 7/2005 | Assmann | A61B 5/0263 | 324/306 |
| 2006/0052698 A1 * | 3/2006 | Loupas | A61B 8/06 | 600/437 |
| 2007/0043294 A1 * | 2/2007 | Li | A61B 8/06 | 600/455 |
| 2007/0208263 A1 * | 9/2007 | John | A61B 5/0452 | 600/509 |
| 2008/0059098 A1 * | 3/2008 | Zhang | G01S 7/52077 | 702/103 |
| 2009/0015587 A1 * | 1/2009 | Hashimoto | A61B 8/06 | 345/424 |
| 2009/0024037 A1 * | 1/2009 | Baba | A61B 8/06 | 600/454 |
| 2009/0067699 A1 | 3/2009 | Clark | | |
| 2010/0069757 A1 * | 3/2010 | Yoshikawa | A61B 5/02007 | 600/454 |
| 2010/0324424 A1 * | 12/2010 | Sato | A61B 8/06 | 600/454 |
| 2011/0150309 A1 * | 6/2011 | Barfett | G06T 7/33 | 382/131 |
| 2011/0301470 A1 * | 12/2011 | Sato | A61B 8/06 | 600/463 |
| 2012/0078108 A1 * | 3/2012 | Kim | A61B 8/06 | 600/454 |
| 2012/0136248 A1 | 5/2012 | Kanayama et al. | | |
| 2012/0172725 A1 * | 7/2012 | Wang | A61B 8/06 | 600/443 |
| 2012/0201031 A1 * | 8/2012 | Marley | G02B 27/0006 | 362/294 |
| 2013/0150717 A1 * | 6/2013 | Sato | A61B 8/06 | 600/441 |
| 2013/0281855 A1 * | 10/2013 | Baba | A61B 8/06 | 600/441 |
| 2014/0121476 A1 * | 5/2014 | Tran | A61B 5/0024 | 600/301 |
| 2014/0358000 A1 * | 12/2014 | Gupta | A61B 8/06 | 600/441 |
| 2014/0371594 A1 * | 12/2014 | Flynn | G01S 15/8984 | 600/454 |
| 2015/0011882 A1 * | 1/2015 | Abe | G01S 15/8995 | 600/443 |
| 2015/0282787 A1 * | 10/2015 | Sato | A61B 8/06 | 600/441 |
| 2015/0320481 A1 * | 11/2015 | Cosman, Jr. | A61B 18/1482 | 606/35 |
| 2015/0359507 A1 * | 12/2015 | Shibata | A61B 8/06 | 600/443 |
| 2016/0151038 A1 * | 6/2016 | Govinahallisathyanarayana | G01S 15/8979 | 600/454 |
| 2016/0157826 A1 * | 6/2016 | Sisodia | B06B 1/0215 | 600/454 |
| 2019/0388065 A1 | 12/2019 | Flynn et al. | | |

FOREIGN PATENT DOCUMENTS

| | | | |
|---|---|---|---|
| CN | 102525564 A | 7/2012 | |
| CN | 102686164 A | 9/2012 | |
| CN | 104011559 A | 8/2014 | |
| CN | 104095656 A | 10/2014 | |
| JP | 11033024 A * | 2/1999 | A61B 8/08 |
| JP | 2005-500888 A | 1/2005 | |
| WO | 00/40996 A1 | 7/2000 | |
| WO | 01/75476 A1 | 10/2001 | |
| WO | 2013/059659 A1 | 4/2013 | |

OTHER PUBLICATIONS

Communication dated Nov. 27, 2015 issued by Korean Intellectual Property Office in counterpart Korean Patent Application No. 10-2014-0177827.

Office Action dated Jun. 18, 2019 by the State Intellectual Property Office of P.R. China in counterpart Chinese Patent Application No. 201510543841.1.

(56) References Cited

OTHER PUBLICATIONS

Communication dated Feb. 25, 2020 from the State Intellectual Property Office of the P.R.China. in application No. 201510543841.1.

* cited by examiner

ULTRASOUND DIAGNOSIS APPARATUS AND METHOD OF OPERATING THE SAME

RELATED APPLICATIONS

This application claims the benefit of U.S. Provisional Application No. 62/044,374, filed on Sep. 1, 2014, in the U.S. Patent Office and Korean Patent Application No. 10-2014-0177827, filed on Dec. 10, 2014, in the Korean Intellectual Property Office, the disclosures of which are incorporated herein in their entireties by reference.

BACKGROUND

1. Field

One or more exemplary embodiments relate to an ultrasound diagnosis apparatus and method of operating the same, and more particularly, to an ultrasound diagnosis apparatus and method of operating the same, which are capable of providing an optimized color flow image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

An ultrasound diagnosis apparatus may operate in a brightness (B) mode, a Doppler mode, an elastic mode, and the like. In the B mode, a reflection coefficient of an ultrasound signal is visualized as a two-dimensional (2D) image. In the Doppler mode, a velocity of a moving object (in particular, blood flow) is shown as an image by using the Doppler effect. In the elastic mode, a difference between responses when compression is or not applied to an object is visualized as an image.

SUMMARY

One or more exemplary embodiments include an ultrasound diagnosis apparatus and a method of operating the same, which are capable of providing an optimized color flow image by automatically setting in real-time a parameter necessary for generating a color flow image.

Additional aspects will be set forth in part in the description which follows and, in part, will be apparent from the description, or may be learned by practice of the presented exemplary embodiments.

According to one or more exemplary embodiments, an ultrasound diagnosis apparatus includes: a data acquisition unit configured to acquire flow data in real-time from a region of interest (ROI) of an object; a parameter setting unit configured to analyze a change in blood flow based on the flow data acquired in real-time and set a parameter according to the analyzed change in blood flow; an image generator configured to generate a color flow image of the ROI by applying the set parameter to the flow data; and a display configured to display the color flow image.

The flow data may include at least one of power data, velocity data, and variance data of the blood flow through the ROI.

The parameter may include at least one of a power threshold, a power ceiling, a velocity threshold, a velocity ceiling, a scale, and a baseline.

The parameter setting unit may generate a histogram based on the flow data and analyzes the histogram, thereby setting the parameter.

The parameter setting unit may set the parameter by analyzing spatial distribution of the flow data.

The parameter setting unit may set a power threshold to increase as a value of power data of blood flow through the ROI increases and to decrease as the value of the power data decreases.

The image generator may generate the color flow image by using power data that has a value that is greater than or equal to a set power threshold among power data of blood flow through the ROI.

The display may display the color flow image by overlapping the color flow image on a brightness (B) mode image of the object The ultrasound diagnosis apparatus may further include a user input unit configured to receive a user input for selecting an automatic mode in which the parameter is automatically set.

According to one or more exemplary embodiments, a method of operating an ultrasound diagnosis apparatus includes: acquiring flow data in real-time from an ROI of an object; analyzing a change in blood flow based on the flow data acquired in real-time and setting a parameter according to the analyzed change in blood flow; generating a color flow image of the ROI by applying the set parameter to the flow data; and displaying the color flow image.

In the setting of the parameter, a histogram may be generated based on the flow data, and the parameter is set by analyzing the histogram.

In the setting of the parameter, the parameter may be set by analyzing spatial distribution of the flow data.

In the setting of the parameter, a power threshold may be set to increase as a value of power data of blood flow through the ROI increases and to decrease as the value of the power data decreases.

In the generating of the color flow image, the color flow image may be generated by using power data that has a value that is greater than or equal to a set power threshold among power data of blood flow through the ROI.

In the displaying of the color flow image, the color flow image may be displayed by overlapping the color flow image on a brightness (B) mode image of the object.

According to the exemplary embodiments, an optimized color flow image may be generated by automatically setting a parameter necessary for generating a color flow image in real-time.

Furthermore, the user does not need to set a parameter directly or input a parameter via a predetermined button according to a view in which blood flow is being measured, thus enhancing user convenience.

In addition, a parameter is set based on flow data, thus increasing the accuracy of a color flow image.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These

DETAILED DESCRIPTION

Figure 1:
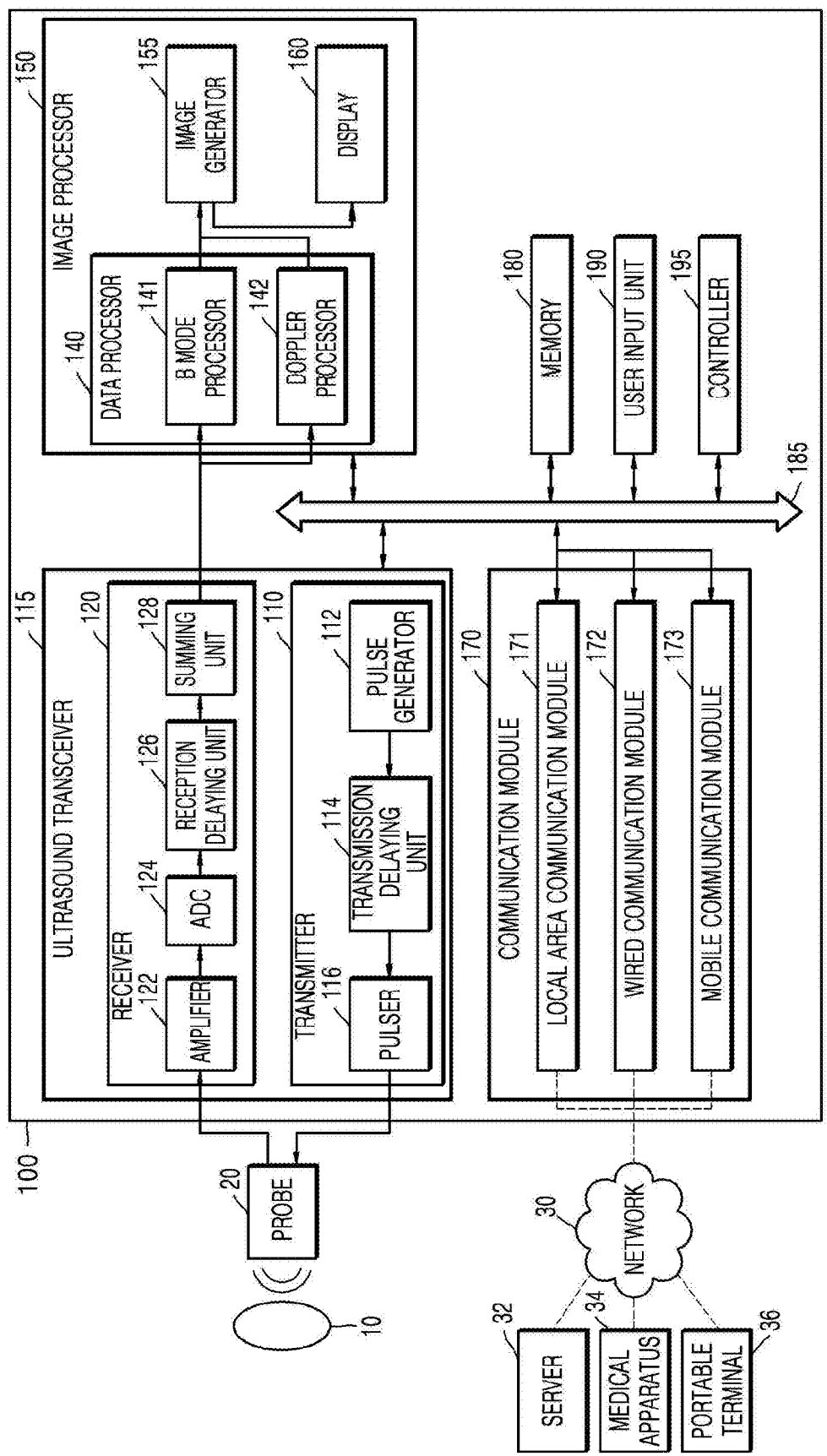
FIG. 1 is a block diagram of a configuration of an ultrasound diagnosis apparatus according to an exemplary embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Furthermore, an ultrasound image may take different forms. For example, the ultrasound image may be at least one selected from an amplitude (A) mode image, a brightness (B) mode image, a color (C) mode image, and a Doppler (D) mode image. In addition, according to an exemplary embodiment, the ultrasound image may be a two-dimensional (2D) or three-dimensional (3D) image.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to exemplary embodiments, examples of which are illustrated in the accompanying drawings, wherein like reference numerals refer to like structural elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

FIG. 1 is a block diagram of a configuration of an ultrasound diagnosis apparatus 100 according to an exemplary embodiment.

Referring to FIG. 1, the ultrasound diagnosis apparatus 100 may include a probe 20, an ultrasound transceiver 115, an image processor 150, a communication module 170, a memory 180, a user input unit 190, and a controller 195, which may be connected to one another via buses 185. In addition, the image processor 150 may include a data processor 140, an image generator 155, and a display 160

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 115 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly.

A transmitter 110 supplies a driving signal to the probe 20. The transmitter 1110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 1124 by delay times necessary for determining reception directionality, and the summing unit 128 generates ultrasound data by summing the echo signals processed by the reception delaying unit 126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 150 generates an ultrasound image by scan-converting ultrasound data generated by the ultrasound transceiver 115 and displays the ultrasound image.

The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color flow image), a tissue Doppler image showing a movement of tissue, or a spectral Doppler image showing a moving speed of an object as a waveform.

A B mode processor 141 extracts B mode components from ultrasound data and processes the B mode components. An image generator 155 may generate an ultrasound image indicating signal intensities as brightness based on the extracted B mode components.

Similarly, a Doppler processor 142 may extract Doppler components from ultrasound data, and the image generator 155 may generate a Doppler image (e. g., a color flow image, etc.) indicating a movement of an object as colors or waveforms based on the extracted Doppler components.

According to an exemplary embodiment, the Doppler processor 142 may set a parameter based on flow data among ultrasound data. The flow data may include at least one selected from power data representing blood flow power, velocity data representing a blood flow velocity, and variance data representing blood flow variance.

Furthermore, to generate a color flow image, the parameter may include a parameter that is applied to color flow data. For example, the parameter may include a power threshold or power ceiling that is applied to blood flow power data, a velocity threshold or velocity ceiling that is applied to blood flow velocity data, a scale of a color flow image, and a baseline.

The Doppler processor 142 may analyze blood flow power data to set a power threshold or power ceiling that is applied to the blood flow power data. The Doppler processor 142 may also analyze blood flow velocity data to set a velocity threshold or velocity ceiling that is applied to the blood flow velocity data. However, exemplary embodiments are not limited thereto, and the Doppler processor 142 may set the parameter necessary for generating a color flow image based on at least one selected from blood flow power data, blood flow velocity data, and blood flow variance data.

According to an embodiment, the image generator 155 may generate a three-dimensional (3D) ultrasound image via volume-rendering with respect to volume data and may also generate an elasticity image by imaging deformation of the object 10 due to pressure.

The image generator 155 may also generate a color flow image by applying the parameter set by the Doppler processor 142 to flow data. The color flow image may show information about movement of an object such as blood flow in a color.

Furthermore, the image generator 155 may display various pieces of additional information in an ultrasound image by using text and graphics. In addition, the generated ultrasound image may be stored in the memory 180.

The display 160 displays the generated ultrasound image. The display 160 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 160 according to embodiments.

The display 160 may include at least one of a liquid crystal display (LCD), a thin film transistor-LCD (TFT-LCD), an organic light-emitting diode (OLED) display, a flexible display, a 3D display, and an electrophoretic display.

Furthermore, when the display 160 and a user input unit form a layer structure to form a touch screen, the display 1600 may be used as an input device as well as an output device, via which a user inputs information via a touch.

The touch screen may be configured to detect a position of a touch input, a touched area, and pressure of a touch. The touch screen may also be configured to detect both an actual touch and a proximity touch.

In the present specification, an 'actual touch' means that a pointer actually touches a screen, and the term a 'proximity touch' means that a pointer does not actually touch a screen but approaches the screen while being separated from the screen by a predetermined distance. A 'pointer' used herein means a tool for touching a particular portion on or near a displayed screen. Examples of the pointer may include a stylus pen and a body part such as fingers.

Although not shown, various sensors may be disposed within or near the touch screen so as to sense an actual touch or proximity touch on the touch screen. A tactile sensor is an example of the sensors for sensing a touch on the touch screen.

The tactile sensor is used to sense a touch of a particular object to the same or greater degree than the degree to which a human can sense the touch. The tactile sensor may detect various pieces of information including the roughness of a contact surface, the hardness of an object to be touched, the temperature of a point to be touched, etc.

A proximity sensor is another example of the sensors for sensing a touch. The proximity sensor refers to a sensor that senses the presence of an object that is approaching or is located near a predetermined detection surface by using the force of an electromagnetic field or infrared light without mechanical contact Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, an infrared proximity sensor, and the like.

The communication module 170 is connected to a network 30 by wire or wirelessly to communicate with an external device or a server. The communication module 170 may exchange data with a hospital server or another medical apparatus in a hospital, which is connected thereto via a PACS. Furthermore, the communication module 170 may perform data communication according to the digital imaging and communications in medicine (DICOM) standard.

The communication module 170 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 170 may receive information about a diagnosis history or medical treatment schedule of a patient from a server and utilizes the received information to diagnose the patient. Furthermore, the communication module 170 may perform data communication not only with a server or a medical apparatus in a hospital, but also with a portable terminal of a medical doctor or patient.

The communication module 170 is connected to the network 30 by wire or wirelessly to exchange data with a server 32, a medical apparatus 34, or a portable terminal 36. The communication module 170 may include one or more components for communication with external devices. For example, the communication module 170 may include a local area communication module 171, a wired communication module 172, and a mobile communication module 173.

The local area communication module 171 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 172 refers to a module for communication using electric signals or optical signals. Examples of wired communication techniques according to an embodiment may include communication via a twisted pair cable, a coaxial cable, an optical fiber cable, and an Ethernet cable.

The mobile communication module 173 transmits or receives wireless signals to or from at least one selected from a base station, an external terminal, and a server on a mobile communication network. The wireless signals may be voice call signals, video call signals, or various types of data for transmission and reception of text/multimedia messages.

The memory 180 stores various data processed by the ultrasound diagnosis apparatus 100. For example, the memory 180 may store medical data related to diagnosis of an object, such as ultrasound data and an ultrasound image that are input or output, and may also store algorithms or programs which are to be executed in the ultrasound diagnosis apparatus 100.

The memory 180 may be any of various storage media, e.g., a flash memory, a hard disk drive, EEPROM, etc. Furthermore, the ultrasound diagnosis apparatus 100 may utilize web storage or a cloud server that performs the storage function of the memory 180 online.

The user input unit 190 generates input data that is received for controlling an operation of the ultrasound diagnosis apparatus 100. The user input unit 190 may include hardware components, such as a keypad, a mouse, a touch pad, and a jog switch. However, exemplary embodiments are not limited thereto, and the user input unit 190 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc. In particular, the user input unit 190 may also include a touch screen in which a touch pad forms a layer structure with the display 160.

In this case, according to an exemplary embodiment, the ultrasound diagnosis apparatus 100 may display an ultrasound image in a predetermined mode and a control panel for the ultrasound image on a touch screen. The ultrasound diagnosis apparatus 100 may sense a user's touch gesture performed on an ultrasound image via a touch screen. The ultrasound diagnosis apparatus 100 may include as physical buttons some buttons that are frequently used by a user among buttons that are included in a control panel of a general ultrasound apparatus, and provide the remaining buttons in the form of a GUI via a touch screen.

According to an exemplary embodiment, the user input unit 190 may include a button for selecting one of an automatic mode for automatically selecting a parameter (necessary for generating a color flow image) and a manual mode for manually setting the parameter based on a user input. However, exemplary embodiments are not limited thereto, and the user input unit 190 may be implemented in various other forms such as a switch, a key, and the like.

The controller 195 may control all operations of the ultrasound diagnosis apparatus 100. In other words, the controller 195 may control operations among the probe 20, the ultrasound transceiver 115, the image processor 150, the communication module 170, the memory 180, and the user input unit 190 shown in FIG. 2.

All or some of the probe 20, the ultrasound transceiver 115, the image processor 150, the communication module 170, the memory 180, the user input unit 190, and the controller 195 may be implemented as software modules. However, exemplary embodiments are not limited thereto, and some of the components stated above may be implemented as hardware modules. Furthermore, at least one selected from the ultrasound transceiver 115, the image processor 150, and the communication module 170 may be included in the controller 195. However, exemplary embodiments are not limited thereto.

Figure 2:
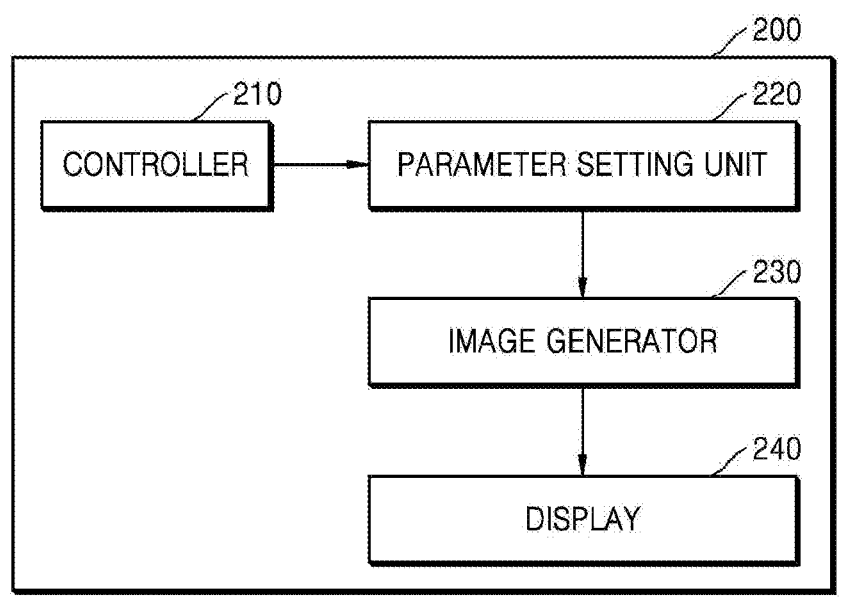
FIG. 2 is a block diagram of a configuration of an ultrasound diagnosis apparatus according to an exemplary embodiment.

FIG. 2 is a block diagram of a configuration of an ultrasound diagnosis apparatus 200 according to an exemplary embodiment. Referring to FIG. 2, the ultrasound diagnosis apparatus 200 according to the present exemplary embodiment may include a data acquisition unit 210, a parameter setting unit 220, an image generator 230, and a display 240.

The data acquisition unit 210 shown in FIG. 2 may correspond to the probe 20 or the ultrasound transceiver 115 shown in FIG. 1. The parameter setting unit 220, the image generator 230, and the display 240 shown in FIG. 2 may respectively correspond to the Doppler processor 142, the image generator 150, and the display 160 shown in FIG. 1.

The data acquisition unit 210 may acquire flow data for a region of interest (ROI).

For example, if the ROI is a blood vessel, the data acquisition unit 210 may acquire at least one selected from power data representing power of blood flow through the blood vessel, velocity data representing a velocity of blood flow, and variance data representing a variance of blood flow.

The data acquisition unit 210 may acquire flow data for an ROI by transmitting an ultrasound signal to the ROI and receiving an echo signal reflected from the ROI. Alternatively, the data acquisition unit 210 may receive flow data from an external device. In this case, the data acquisition unit 210 may receive the flow data from the external device via a communication module. Furthermore, the data acquisition unit 210 may acquire flow data in real-time.

The parameter setting unit 220 may analyze a change in blood flow in real-time based on flow data for the ROI and set parameter according to the analyzed change in blood flow. For example, the change in blood flow may include changes in blood flow amount (power), blood flow velocity, and blood flow distribution.

To generate a color flow image of an ROI, the parameter may include parameter that is applied to flow data. For example, the parameter that is applied to flow data may include a power threshold or power ceiling that is applied to blood flow power data, a velocity threshold or velocity ceiling that is applied to blood flow velocity data, a scale of a color flow image, and a baseline.

The parameter setting unit 220 may analyze power data of blood flow acquired in real-time to set a power threshold or power ceiling that is applied to the power data. Furthermore, the parameter setting unit 220 may analyze velocity data of blood flow acquired in real-time to set a velocity threshold or velocity ceiling that is applied to the velocity data. However, exemplary embodiments are not limited thereto, and the parameter setting unit 220 may set the parameter necessary for generating a color flow image, based on at least one selected from power data, velocity data, and variance data of blood flow that are acquired in real-time.

A power threshold and a power ceiling may be parameters for determining a lower limit and an upper limit for power data, respectively. Similarly, a velocity threshold and a velocity ceiling may be parameters for determining a lower limit and an upper limit for velocity data, respectively. A scale of a color flow image may be a parameter for determining a range of values indicated on the color flow image. A baseline may be a parameter for determining a reference value for values indicated on a color flow image.

The image generator 230 may generate a color flow image of an ROI by using flow data to which a parameter is applied. For example, the image generator 230 may generate a color flow image by using power data that has a value that is greater than or equal to a set power threshold or less than a set power ceiling among power data of blood flow corresponding to the ROI. Alternatively, the image generator 230 may generate a color flow image by using velocity data that has a value that is greater than or equal to a set velocity threshold or less than a set velocity ceiling among velocity data of blood flow corresponding to the ROI.

The display 240 may display a color flow image of an ROI. For example, the display 240 may superimpose a color flow image of a region of an object set as the ROI on a B-mode image of the object for display. However, exemplary embodiments are not limited thereto.

Figure 3:
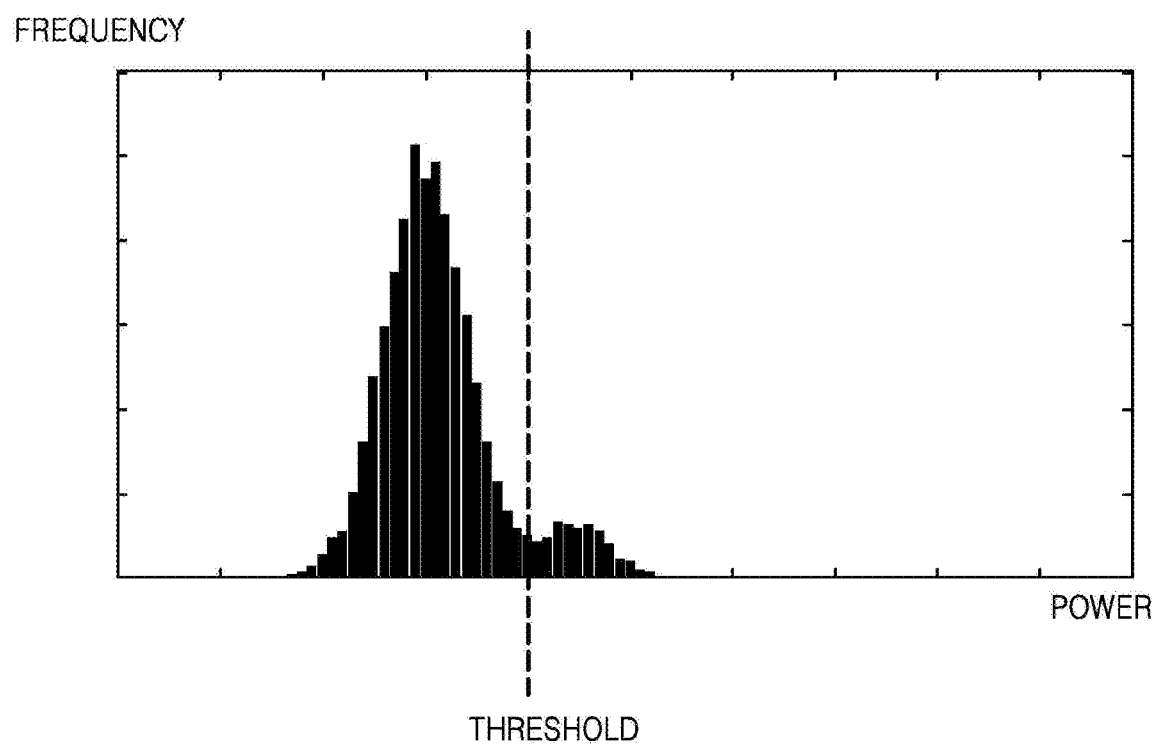
FIGS. 3, 4A and 4B are reference diagrams for explaining a method of generating a color flow image, according to an exemplary embodiment.
Figure 4A:
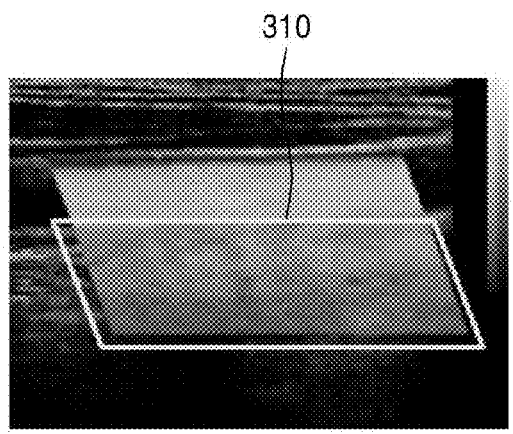
Figure 4B:
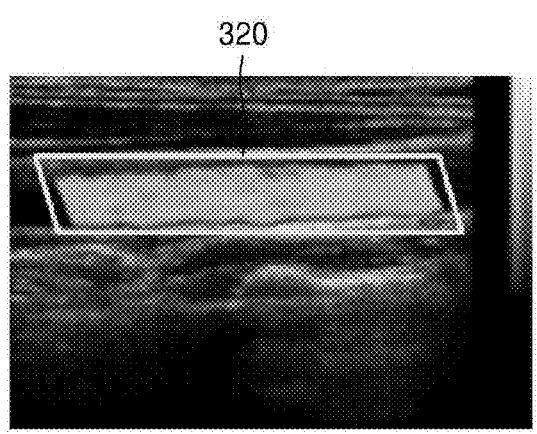

FIGS. 3, 4A and 4B are reference diagrams for explaining a method of generating a color flow image, according to an exemplary embodiment.

FIG. 3 illustrates a histogram for power data of blood flow corresponding to an ROI. As shown in FIG. 3, the ultrasound diagnosis apparatus 100 of FIG. 1 (200 of FIG. 2) may acquire power data of blood flow corresponding to the ROI and generate the histogram for the acquired power data. The abscissa and ordinate of the histogram respectively indicate power values and the frequency of occurrence for each power value.

The parameter setting unit 220 may set a power threshold in real-time according to a change in the amount of blood flow by analyzing a histogram for power data acquired in real-time. For example, the parameter setting unit 220 may set a power threshold by analyzing the spatial distribution of power data. As shown in FIGS. 4A and 4B, other than a blood vessel, the parameter setting unit 220 may set a power threshold value by analyzing power data corresponding to a region 310 outside the blood vessel.

Thus, as shown in FIG. 3, the parameter setting unit 220 may set a first power value as a power threshold and distinguish noise from a signal based on the first power value (power threshold). For example, the ultrasound diagnosis apparatus 100 (200) may determine power values that are less than the first power value as noise, and power values that are greater than or equal to the first power value as effective signals. However, exemplary embodiments are not limited thereto.

FIG. 4A illustrates a color flow image that is generated using power data of blood flow acquired by the data acquisition unit 210. In this case, the color flow image shown in FIG. 4A may be generated using power data acquired without setting a threshold described with reference to FIG. 3.

On the other hand, FIG. 4B illustrates a color flow image generated based on power data (e.g., an effective signal excluding noise) that has a value that is greater than or equal to a power threshold among power values. As seen on FIGS. 4A and 4B, the color flow image of FIG. 4A depicts blood flow not only in a blood vessel but also in the region 310 outside the blood vessel, whereas the color flow image of FIG. 4B indicates blood flow only in a region 320 within a blood vessel.

Although it has been described with reference to FIGS. 3 and 4 that a color flow image is generated by setting a parameter for power data of blood flow, exemplary embodiments are not limited thereto. The above-described method may also be applied in the same way to blood flow velocity data, blood flow variance data, and the like.

Figure 5C:
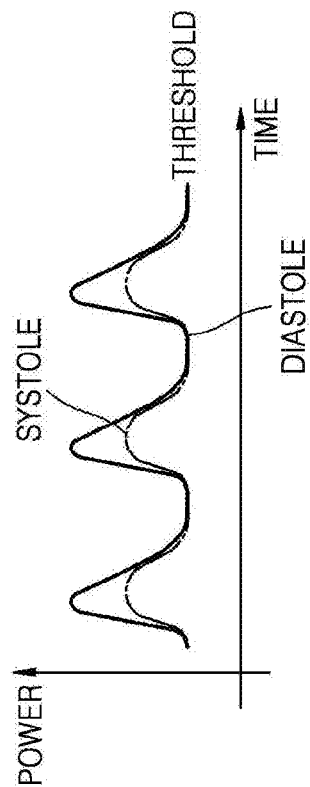
FIGS. 5A through 5D are other reference diagrams for explaining a method of generating a color flow image, according to an exemplary embodiment.
Figure 5D:
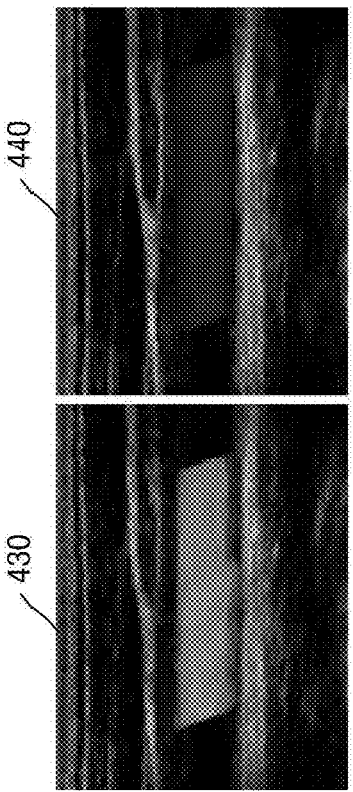
Figure 5A:
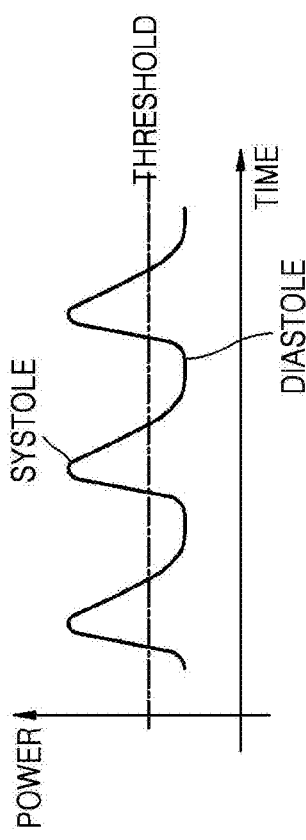

FIGS. 5A through 5D are other reference diagrams for explaining a method of generating a color flow image, according to an exemplary embodiment. FIGS. 5A and 5C are graphs of blood flow power with respect to time and a threshold for blood flow power with respect to time.

The graph of FIG. 5A shows that a threshold for blood flow power is set at a uniform value regardless of a change in blood flow.

Figure 5B:
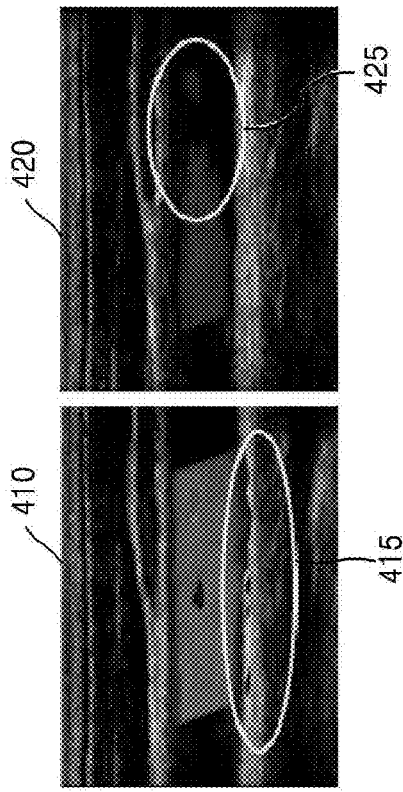

FIG. 5B shows color flow images (first and second images) 410 and 420 respectively corresponding to a systole phase and a diastole phase of the heart when a threshold is set uniformly as shown in FIG. 5A.

Referring to FIG. 5B, since power data of blood flow has a value that is greater than a threshold for blood flow power when the heart is in a systole phase (a blood flow amount is large), the first image 410 depicts blood flow even in a region 415 outside a blood vessel. On the other hand, since power data of blood flow has a value that is less than a threshold for blood flow power when the heart is in a diastole phase (a blood flow amount is small), the second image 420 does not show blood flow in a region 425 within a blood vessel, and thus, the blood flow appears to be disconnected at the region 425.

The graph of FIG. 5C shows that a threshold for blood flow power is set differently according to a change in blood flow.

Referring to FIG. 5C, according to an exemplary embodiment, the parameter setting unit 220 may set a threshold for blood flow power differently based on power data of blood flow acquired in real-time. In this case, a waveform of threshold for blood flow power over time may be similar to a waveform of blood flow power (blood flow amount) over time. Furthermore, a threshold for blood flow power may be set differently according to a change in blood flow amount, and may vary in synchronization with a change in contraction and relaxation of the heart. FIG. 5D shows color flow images (third and fourth images) 430 and 440 respectively corresponding to a systole phase and a diastole phase of the heart when a threshold for blood flow power is set differently as shown in FIG. 5C.

Referring to FIG. 5D, since a threshold for blood flow power is set based on power data of blood flow, the threshold for blood flow power varies over time similarly to power values of blood flow. For example, if a power value of blood flow increases, a threshold for blood flow power may increase. If a power value of blood flow decreases, a threshold for blood flow may decrease. Thus, the third and fourth images 430 and 440 may indicate that blood flow within a blood vessel is constant regardless of whether the heart is in a systole (blood flow amount is large) or diastole phase (blood flow amount is small)

Figure 6A:
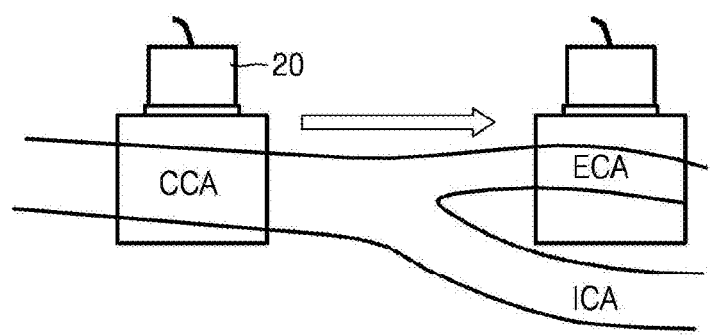
FIGS. 6A and 6B are other reference diagrams for explaining a method of generating a color flow image according to an exemplary embodiment.
Figure 6B:
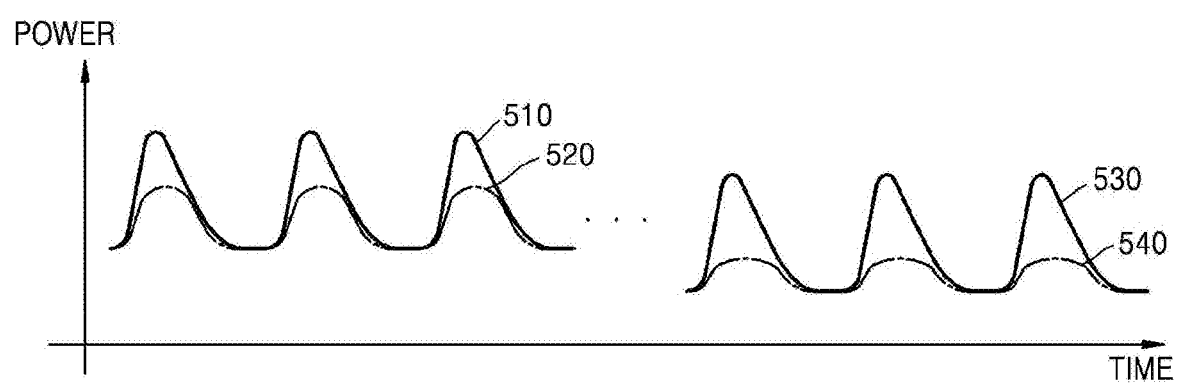

FIGS. 6A and 6B are other reference diagrams for explaining a method of generating a color flow image, according to an exemplary embodiment.

FIG. 6A illustrates an example where flow data corresponding to the Common Carotid Artery (CCA) is acquired and then the probe (20 of FIG. 1) is moved to acquire flow data corresponding to the External Carotid Artery (ECA). FIG. 6B is a graph of blood flow power with respect to time and a threshold for blood flow power with respect to time. In the graph of FIG. 6B, a first blood flow power waveform 510 and a first threshold waveform 520 respectively represent blood flow power and a threshold for blood flow power when power data of blood flow corresponding to CCA is acquired. A second blood flow power waveform 530 and a second threshold waveform 540 respectively represent blood flow power and a threshold for blood flow power when power data of blood flow corresponding to ECA is acquired.

Referring to FIGS. 6A and 6B, the CCA is divided into the ECA and the Internal Carotid Artery (ICA), and intensity of blood flow from the ECA is lower than that of blood flow from the CCA since the ECA is thinner than the CCA. Thus, a mean blood flow power in the ECA is less than a mean blood flow power in the CCA.

The parameter setting unit 220 may set a parameter based on an average value of acquired flow data. For example, the parameter setting unit 220 may set a threshold for blood flow power based on acquired power data of blood flow. Referring to FIG. 6B, the mean blood flow power in the ECA is less than that in the CCA, and accordingly, an average threshold for blood flow power in the ECA is set to be less than an average threshold in the CCA.

As described above, even when intensity of blood flow in an ROI varies, a parameter may be set by taking into account an average value of power data. Thus, the image generator 230 may generate an optimized color flow image.

Figure 7:
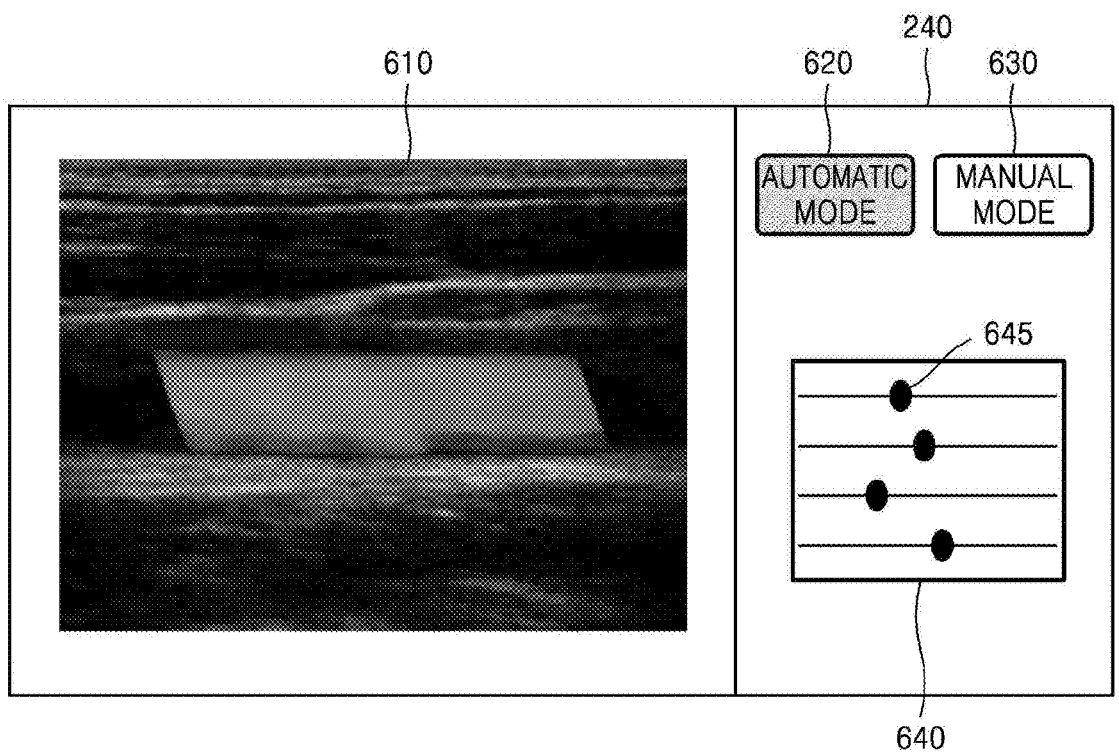
FIG. 7 illustrates an example where a screen for setting an automatic mode and a manual mode is displayed on a display according to an exemplary embodiment.

FIG. 7 illustrates an example where a screen for setting an automatic mode and a manual mode is displayed on the display (240 of FIG. 2) according to an exemplary embodiment Referring to FIGS. 2 and 7, an ultrasound image (e.g., a color flow image) may be displayed on a first region of the display 240, and a user interface 640 for selecting one of an automatic mode and a manual mode may be displayed on a second region of the display 240.

The ultrasound image displayed in the first region may be obtained by overlapping a B-mode image and a color flow image of an ROI on each other. The user interface 640 displayed in the second region may include buttons 620 and 630 for respectively selecting an automatic mode and a manual mode. For example, in the automatic mode, a parameter necessary for generating a color flow image of an ROI may be set automatically based on flow data acquired by the data acquisition unit 210. On the other hand, in the manual mode, a parameter for generating a color flow image of an ROI may be set based on a user input.

For example, if a user selects the automatic mode (touches the button 620), the parameter setting unit 220 may set a parameter automatically based on flow data. In this case, the parameter setting unit 220 may analyze power data of blood flow to set a power threshold or power ceiling that is applied to the power data. The parameter setting unit 220 may also analyze velocity data of blood flow to set a velocity threshold or velocity ceiling that is applied to the velocity data.

Furthermore, according to an exemplary embodiment, while in the automatic mode, the parameter setting unit 220 may automatically set a parameter in real-time based on flow data.

If the user selects the manual mode (touches the button 630), the user may set a parameter by using the user interface 640 for adjusting a parameter value. For example, the user interface 640 may include a plurality of control bars 645 for respectively setting a plurality of parameters.

The user may set a value for a parameter by moving a control bar 645 along a line. For example, if a threshold for power data is set, a larger threshold may be set by locating the control bar 645 for setting the threshold further to the right. A smaller threshold may be set by locating the control bar 645 further to the left.

When the automatic mode is selected, the user interface 640 may be disabled.

The user interface 640 shown in FIG. 7 is a merely an example, and the ultrasound diagnosis apparatus 100 (200) may provide various other user interfaces for setting a parameter.

Figure 8:
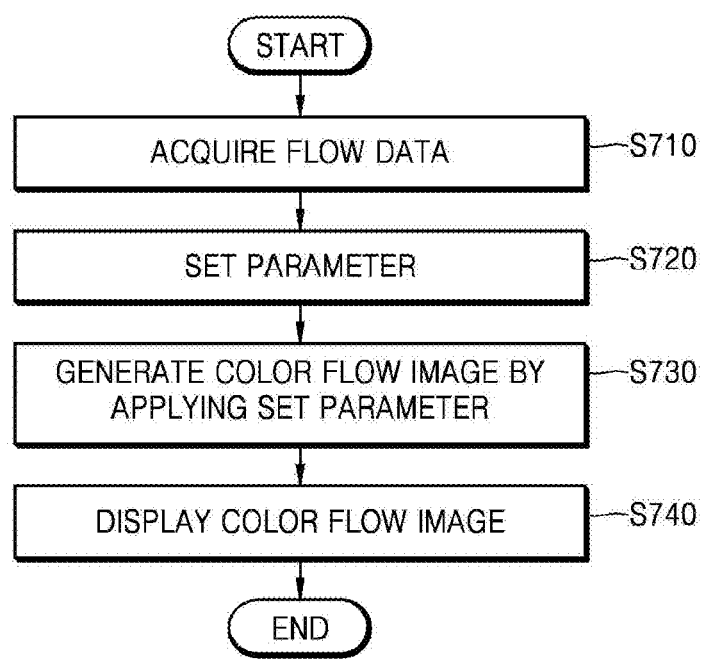
FIG. 8 is a flowchart of a method of operating an ultrasound diagnosis apparatus, according to an exemplary embodiment.

FIG. 8 is a flowchart of a method of operating the ultrasound diagnosis apparatus 100 (200), according to an exemplary embodiment.

Referring to FIGS. 1, 2, and 8, the ultrasound diagnosis apparatus 100 (200) may acquire flow data for an ROI (S710).

The ultrasound diagnosis apparatus 100 (200) may acquire flow data for an ROI by transmitting an ultrasound signal to the ROI and receiving an echo signal reflected from the ROI. Alternatively, the data acquisition unit 210 may receive flow data from an external device. In this case, the flow data may be received from the external device. Furthermore, the data acquisition unit 210 may acquire flow data in real-time.

For example, if the ROI is a blood vessel, the ultrasound diagnosis apparatus 100 (200) may acquire at least one selected from power data representing power of blood flow through the blood vessel, velocity data representing a velocity of blood flow, and variance data representing a variance of blood flow.

The ultrasound diagnosis apparatus 100 (200) may analyze a change in blood flow in real-time based on the flow data and set a parameter corresponding to the ROI according to the analyzed change in blood flow (S720).

For example, the change in blood flow may include changes in blood flow amount (power), blood flow velocity, and blood flow distribution. Furthermore, to generate a color flow image of the ROI, the parameter may include a parameter that is applied to the flow data. For example, the parameter that is applied to the flow data may include a power threshold or power ceiling that is applied to blood flow power data, a velocity threshold or velocity ceiling that is applied to blood flow velocity data, a scale of a color flow image, and a baseline.

A power threshold and a power ceiling may be parameters for determining a lower limit and an upper limit for power data, respectively. Similarly, a velocity threshold and a velocity ceiling may be parameters for determining a lower limit and an upper limit for velocity data, respectively. A scale of a color flow image may be a parameter for determining a range of values indicated on the color flow image.

A baseline may be a parameter for determining a reference value for values indicated on a color flow image.

The ultrasound diagnosis apparatus 100 (200) may analyze power data of blood flow acquired in real-time to set a power threshold or power ceiling that is applied to the power data. Furthermore, the ultrasound diagnosis apparatus 100 (200) may analyze velocity data of blood flow acquired in real-time to set a velocity threshold or velocity ceiling that is applied to the velocity data. However, exemplary embodiments are not limited thereto, and the ultrasound diagnosis apparatus 100 (200) may set the parameter necessary for generating a color flow image, based on at least one selected from power data, velocity data, and variance data of blood flow that are acquired in real-time.

For example, the ultrasound diagnosis apparatus 100 (200) may acquire power data of blood flow corresponding to the ROI and generate the histogram for the acquired power data, with the abscissa and ordinate of the histogram respectively representing blood flow power and the frequency of occurrence for each blood flow power). The ultrasound diagnosis apparatus 100 (200) may extract a power threshold by analyzing the histogram for the power data. However, exemplary embodiments are not limited thereto, and the same method may be applied to blood flow velocity data, blood flow variance data, and the like.

Furthermore, each time the acquired flow data changes, the ultrasound diagnosis apparatus 100 (200) may analyze a change in blood flow based on the changed flow data in real-time and set a parameter according to the analyzed change in blood flow. A waveform of the parameter over time may be similar to a waveform representing a change in blood flow. For example, a waveform of a threshold for blood flow power over time may be similar to a waveform of blood flow power data over time and may vary in synchronization with a change in contraction and relaxation of the heart.

The ultrasound diagnosis apparatus 100 (200) may use the flow data to which the parameter is applied to generate a color flow image of the ROI (S730).

For example, the ultrasound diagnosis apparatus 100 (200) may generate a color flow image by using power data that has a value that is greater than or equal to a set power threshold or less than a set power ceiling, among power data of blood flow corresponding to the ROI. Alternatively, the ultrasound diagnosis apparatus 100 (200) may generate a color flow image by using velocity data that has a value that is greater than or equal to a set velocity threshold or less than a set velocity ceiling among velocity data of blood flow corresponding to the ROI.

The ultrasound diagnosis apparatus 100 (200) may display a color flow image of the ROI (S740).

For example, the ultrasound diagnosis apparatus 100 (200) may overlap a B-mode image of an object and a color flow image of a region of the object set as the ROI on each other for display. However, exemplary embodiments are not limited thereto.

Methods of operating an ultrasound diagnosis apparatus according to the exemplary embodiments may be embodied as a computer-readable code on a computer-readable recording medium. The computer-readable recording medium is any data storage device that can store data which can be thereafter read by a computer system. Examples of computer-readable recording media include read-only memory (ROM), random-access memory (RAM), CD-ROMs, magnetic tapes, floppy disks, optical data storage devices, transmission media such as Internet transmission media, etc. The computer-readable recording media can also be distributed over network-coupled computer systems so that computer-readable codes are stored and executed in a distributed fashion.

While one or more exemplary embodiments have been described with reference to the figures, it will be understood by one of ordinary skill in the art that various changes in form and details may be made therein without departing from the spirit and scope of the present inventive concept as defined by the following claims. That is, all changes and modifications within the scope of the appended claims and their equivalents will be construed as being included in the present inventive concept.

What is claimed is:

1. An ultrasound diagnosis apparatus comprising:
an ultrasound probe configured to acquire flow data in real-time from a region of interest (ROI) of an object, the object comprising an organ, a blood vessel, or a combination thereof, or a phantom;
a Doppler processor configured to analyze power data of blood flow by using the flow data, generate a histogram of the power data of blood flow in real-time indicating a frequency of occurrence for each power value, set a power threshold according to a change in an amount of the blood flow by analyzing the histogram, determine power values that are less than the power threshold as noise, and determine power values that are greater than or equal to the power threshold as effective signals, wherein the power threshold is a parameter for determining a lower limit for the power data;
an image processor configured to generate a color flow image of the ROI by using the effective signals, excluding the noise; and
a display configured to display the color flow image,
wherein the Doppler processor is further configured to adjust the power threshold to increase in real-time as an amount of blood flow through the ROI increases in real-time and to decrease in real-time as the amount of the blood flow through the ROI decreases in real-time.

2. The ultrasound diagnosis apparatus of claim 1, wherein the flow data comprises at least one of power data, velocity data, and variance data of the blood flow through the ROI.

3. The ultrasound diagnosis apparatus of claim 1, wherein the Doppler processor is further configured to set at least one of a velocity threshold, a velocity ceiling, a scale, and a baseline.

4. The ultrasound diagnosis apparatus of claim 1, wherein the Doppler processor is further configured to set the power threshold by analyzing spatial distribution of the power data.

5. The ultrasound diagnosis apparatus of claim 1, wherein the display displays the color flow image by overlapping the color flow image on a brightness (B) mode image of the object.

6. The ultrasound diagnosis apparatus of claim 1, further comprising a user input unit configured to receive a user input for selecting an operating mode from among an automatic mode and a manual mode,
wherein the power threshold and is automatically set when the automatic mode is selected by a user, and the power threshold is set based on a user input for adjusting the power threshold through the user input unit when the manual mode is selected by the user.

7. A method of operating an ultrasound diagnosis apparatus, the method comprising:
acquiring flow data in real-time from a region of interest (ROI) of an object, the object comprising an organ, a blood vessel, or a combination thereof, or a phantom;

analyzing power data of blood flow by using the flow data acquired in real-time;

generating a histogram of the power data of blood flow in real-time indicating a frequency of occurrence for each power value;

setting a power threshold according to a change in an amount of the blood flow by analyzing the histogram, wherein the power threshold is a parameter for determining a lower limit for the power data;

determining power values that are less than the power threshold as noise, and determining power values that are greater than or equal to the power threshold as effective signals;

generating a color flow image of the ROI by using the effective signals, excluding the noise; and displaying the color flow image, wherein, in the setting of the power threshold, the power threshold is adjusted to increase in real-time as an amount of blood flow through the ROI increases in real-time and to decrease in real-time as the amount of the blood flow through the ROI decreases in real-time.

8. The method of claim 7, wherein the flow data comprises at least one of power data, velocity data, and variance data of the blood flow through the ROI.

9. The method of claim 7, wherein the setting the power threshold comprises setting at least one of a velocity threshold, a scale, and a baseline.

10. The method of claim 7, wherein, in the displaying of the color flow image, the color flow image is displayed by overlapping the color flow image on a brightness (B) mode image of the object.

11. The method of claim 7, further comprising receiving a user input for selecting an operating mode from among an automatic mode and a manual mode, wherein the power threshold is automatically set when the automatic mode is selected by a user, and the power threshold is set based on a user input for adjusting the power threshold when the manual mode is selected by the user, the power threshold when the manual mode is selected by the user.

* * * * *